(12) United States Patent
Warrenburg et al.

(10) Patent No.: US 7,264,830 B2
(45) Date of Patent: Sep. 4, 2007

(54) PROCESS FOR EFFECTING THE RELAXATION OF MUSCLES OF A HUMAN BY MEANS OF FRAGRANCE (75) Inventors: William Stephen Warrenburg, Little Silver, NJ (US); Carol M. Christensen, Metuchen, NJ (US); Murray Moscona, Rumson, NJ (US); Anne-Sophie Chapuis-Fournier, Bois-Colombes (FR)

(73) Assignee: International Flavors & Fragrances, Inc., New York, NY (US)

( * ) Notice: Subject to any disclaimer, the term of this patent is extended or adjusted under 35 U.S.C. 154(b) by 0 days.

(21) Appl. No.: 11/383,825

(22) Filed: Jun. 26, 2006

(65) Prior Publication Data

US 2006/0240131 A1 Oct. 26, 2006

Related U.S. Application Data (60) Division of application No. 10/324,930, filed on Dec. 20, 2002, now Pat. No. 7,097,863, which is a continuation-in-part of application No. 10/219,903, filed on Aug. 15, 2002, now abandoned.

(51) Int. Cl.
*A61K 36/00* (2006.01)

(52) U.S. Cl. .................................................. 424/725

(58) Field of Classification Search .................. None
See application file for complete search history.

(56) References Cited

FOREIGN PATENT DOCUMENTS

WO    WO 01/24807 A2 *    4/2001

\* cited by examiner

*Primary Examiner*—Susan Hoffman
(74) *Attorney, Agent, or Firm*—Elizabeth M. Quirk; Joseph F. Leightner (57) ABSTRACT Described is a process for effecting the relaxation of a tensive back, shoulder or neck muscle of a human mammal for a substantial period of time. The process of our invention consists essentially of the step of continuously or periodically administering to said human mammal through inhalation over a stress reactivity-reducing, tensive back, shoulder or neck muscle-relaxing period of time, a stress reactivity-reducing, tensive back, shoulder or neck muscle-relaxing quantity and concentration of one or more fragrance compositions having an aroma profile including one or more of a rose, floral, musky, ambery, sweet and/or powdery aroma notes.

5 Claims, 7 Drawing Sheets

PROCESS FOR EFFECTING THE RELAXATION OF MUSCLES OF A HUMAN BY MEANS OF FRAGRANCE

RELATED APPLICATIONS

This application is a divisional application of U.S. application Ser. No. 10/324,930, filed Dec. 20, 2002, now U.S. Pat. No. 7,097,863, which is a continuation-in-part of U.S. application Ser. No. 10/219,903, filed Aug. 15, 2002, now abandoned.

FIELD OF THE INVENTION

Our invention relates to a process for effecting the relaxation (i) to a substantially low stress-reactive state and (ii) to a substantially low tensive state, of at least one stress-reactive and tensive back, shoulder or neck muscle of a human mammal for a substantial period of time. The process of our invention consists essentially of the step of continuously or periodically administering to said human mammal through inhalation over a stress reactivity-reducing, tensive back, shoulder and/or neck muscle-relaxing period of time, a stress reactivity-reducing, tensive back, shoulder and/or neck muscle-relaxing quantity and concentration of one or more fragrance compositions having an aroma profile including at least one rose, floral, musky, ambery, sweet and/or powdery aroma nuance(s).

BACKGROUND OF THE INVENTION

Reactivity to stress is insidious because it does not directly incapacitate a human, but acts as a vector of extreme discomfort in various locations of the body of the human, e.g., back, shoulder and/or neck muscle pain and spasms which are a direct result of excessive back, shoulder and/or neck muscle tension brought about by the reactivity to stress.

The term "stress" hereinafter refers to an event or experience in life of an individual that has specific physiologic and/or subjective consequences that disturb the equilibrium of the individual (see Kopin, I. J., Definitions of Stress and Sympathetic Neuronal Responses Stress: Basic Mechanisms and Clinical Implications, Annals of the NY Academy of Sciences, G. Chrousos, R. McCarty, K. Pacak et al editors, New York, N.Y., New York Academy of Sciences 771: 19-30.). Sources of stress may be an individual's occupation or it may be a life event such as a change of job. The term "reactivity" hereinafter refers to the change generated by stress in the individual's physiologic and/or subjective condition. Within the context of this invention, the term "reactivity" may be ascertained (a) objectively, by measuring, using electrical measuring techniques, the degree of muscular back, shoulder and/or neck tension and (b) subjectively by use of self-report of various symptoms including degree of muscular back and/or neck pain and degree of muscular back and/or neck 'tension' and 'relaxation'. Unlike a drug that is ingested orally or injected subcutaneously, the fragrance compositions utilized in the practice of our invention are inhaled. Hence, for the purpose of practicing this invention, the term "amount administered" hereinafter is intended to mean "amount of stress reactivity-reducing composition calculated to have been inhaled, retained, absorbed and/or provided into the blood-stream".

Methods for reducing physiological and/or subjective reactivity to stress in humans being subjected to stress conditions by administration of stress reactivity-reducing substances such as nutmeg oil, orange oil and valerian oil through inhalation are well known in the prior art, for example, Warren et al, U.S. Pat. No. 4,671,959 issued on Jun. 9, 1987 and France et al. PCT Published Patent Application WO 00/37092 published on Jun. 29, 2000 (corresponding to Provisional Application for U.S. Letters Patent Ser. No. 60/113,347 filed Dec. 21, 1998). The Warren et al patent and the France et al. published patent application does not disclose or suggest the method of inhalation therapy to induce muscle relaxation, and furthermore, no disclosure of back, shoulder and/or neck muscle relaxation is set forth therein.

In addition, Librizzi et al. PCT Published Patent Application WO 01/24807 (corresponding to Provisional Application for U.S. Letters Patent Ser. No. 60/157,371 filed on Oct. 1, 1999) discloses a method of calming a mammal by administering to said mammal a personal care composition which comprises an effective amount of a sensory fragrance wherein the personal care composition is capable of reducing the cortisol level of the mammal by about 0.1% up to about 75% and/or increasing the sigA level of the mammal by from about 10% up to about 150%. Although Librizzi et al. indicates at page 3: "The term 'administering' refers to (i) inhalation of a topically applied personal care composition . . . ", the Librizzi et al. published PCT Patent Application does not, however disclose or suggest the method of inhalation therapy to induce muscle relaxation, and furthermore, no disclosure or suggestion of any methods for the causation of back, shoulder and/or neck muscle relaxation or significant reduction of back, shoulder or neck muscle tension is set forth therein.

The use of "Kava" (Piper methysticum) and Valerian (Valeriana officinalis) to induce muscle relaxation is disclosed by Greadon, J. and Graedon, T. in "The People's Pharmacy Guide to Home and Herbal Remedies",© 1999 by Graedon Enterprises, Inc., at pages 335-337, and 375-377; Published by St. Martin's Press, New York, N.Y. The Graedon et al publication does not disclose or suggest the method of inhalation therapy to induce muscle relaxation, and furthermore, no disclosure or suggestion of back, shoulder and/or neck muscle relaxation is set forth therein.

The use of oil of wintergreen (methyl salicylate), rosemary, aspic, juniper, lavender, nutmeg, pepper, mandarin, neroli, petitgrain, fennel, pine and thyme are disclosed as being useful in reduction of muscular pain by Daniele Ryman in "Aromatherapy: The Complete Guide to Plant and Flower Essences for Health and Beauty",© 1991 by Daniele Ryman at pages 242, 243, 244, 268, 269, 308, 335, 344 and 345; Published, 1991 by Piatkus Books. The Ryman publication does not disclose or suggest the method of inhalation therapy to induce muscle relaxation, and furthermore, no disclosure of back, shoulder and/or neck muscle relaxation is set forth therein.

The use of essential oils including Clary Sage and Jasmine in massage and baths is disclosed to have a relaxing effect on the muscles by Davis, P. in "Aromatherapy An A-Z",© Patricia Davis 1988, at pages 230 and 231; Published 1988 by The C. W. Daniel Company Limited, Saffron Walden, Essex, England. The Davis publication does not disclose or suggest the method of inhalation therapy to induce muscle relaxation, and furthermore, no disclosure or suggestion of back, shoulder and/or neck muscle relaxation is set forth therein.

Reduction of muscle tension "mainly neck and shoulders" by means of application via massage of:
*Chamaemelum nobile*
*Juniperus communis*
*Lavandula augustifolia*

*Lavandula X intermedia* 'Super'
*Origanum marjorana* and
*Eucalyptus smithii* [GULLY GUM]

is disclosed by Price, S. and Price, L. in "*Aromatherapy for Health Professionals*"© Harcourt Publishers Limited 1999, Chapter 12, "Stress", pages 207-215. The Price, et al. publication does not, however, explicitly or implicitly disclose the method of inhalation therapy to induce muscle relaxation.

Accordingly, a need exists for a process for effecting the relaxation to (i) a substantially non stress-reactive state and (ii) a substantially non-tensive state of at least one stress-reactive and tensive back, shoulder or neck muscle of a human mammal for a substantial period of time, using one or more specifically-designed fragrance compositions to be conveniently administered by means of inhalation.

SUMMARY OF THE INVENTION

Our invention is directed to a process for effecting the relaxation to (i) a substantially low stress-reactive state and (ii) a substantially low tensive state, of at least one stress-reactive and tensive back, shoulder or neck muscle of a human mammal for a substantial period of time. Such back, shoulder or neck muscles include, but are not limited to upper layer muscles such as the Splenius capitis muscle, the Splenius cervicus muscle, the Levator scapulae muscle, the Rhomboid major muscle, the Supraspinatus muscle, the Erector spinae muscle, the Trapezius muscle, the Serratus anterior muscle and the External oblique muscle; intermediate layer muscles such as the Rectus capitis posterior major muscle, the Longissimus captis muscle, the Spinalis thoracis muscle and the Iliocostalis lumborum muscle; and the deep layer muscles such as the Rectus capitis posterior minor muscle, the Interspinalis cervicis muscle, the Levator costae muscle, the Longus rotatores thoracis muscle, and the Quadratus lumborum muscle. The process of our invention consists essentially of the step of continuously or periodically administering to said human mammal through inhalation over a stress reactivity-reducing, tensive back, shoulder and/or neck muscle-relaxing period of time, a stress reactivity-reducing, tensive back, shoulder and/or neck muscle-relaxing quantity and concentration of one or more fragrance compositions having an aroma profile including at least one rose, floral, musky, ambery, sweet and/or powdery aroma fragrance notes or nuances.

More particularly, our invention is directed to a process for effecting the relaxation to (i) a substantially low stress-reactive state and (ii) a substantially low tensive state of at least one (M) stress-reactive and tensive back, shoulder or neck muscle of a human mammal having a weight, W, of from about 50 pounds up to about 300 pounds, each of which back or neck muscle has an initial magnitude of tension, $\delta_{io}$ microvolts, in the range of from about 0.5 microvolts up to about 10.0 microvolts for a substantial period of time, $\Delta\theta$, preferably from about 1 minute up to about 24 hours, consisting essentially of the step of continuously or periodically administering to said human mammal through inhalation over a stress reactivity-reducing, tensive back, shoulder or neck muscle-relaxing period of time, $(\Delta\theta)'$, preferably from about 1 minute up to about 24 hours, a stress reactivity-reducing, tensive back, shoulder or neck muscle-relaxing (i) quantity, Q, preferably from about 6.0 nanograms up to about 500 micrograms; (ii) concentration, C, preferably from about 1 nanogram per liter up to about 125 micrograms per liter and (iii) inhalation rate, $\partial Q/\partial\theta$, (the partial derivative of quantity of fragrance inhaled with respect to time of inhalation) preferably from about 1 microgram/hour up to about 45 milligrams/hour, of one or more fragrance compositions of matter having an aroma profile selected from the group consisting of rose, floral, musky, ambery, sweet and powdery, wherein the resulting relaxation effect has a magnitude R>10 on a scale of 1-100 and the resulting magnitude of back, neck and/or shoulder muscle tension, $\delta_{if}$ is in the range of from about 0.4 microvolts up to about 3.3 microvolts and wherein $\delta_{io}$ is greater than at least about 1.05 $\delta_{if}$ microvolts, preferably greater than about 1.10 $\delta_{if}$ microvolts, and most preferably greater than about 1.25 $\delta_{if}$ microvolts.

Other preferred embodiments of the present invention include the use of fragrance for immediate relief by providing fragrance in higher concentration for a short period of time to longer lasting applications where fragrance at a lower dosage is provided for extended periods of time. Fragrance may be provided in duration as short as about 30 seconds to as long as about 24 hours, preferably such as from about 2 minutes to about three hours. The amount of fragrance provided can be at levels ranging from about 1 microgram to about 100, preferably from about 10 to about 50 micrograms/liter of air inhaled by the subject.

The aforementioned process may be further defined as involving a mathematical relationship wherein $$R = f(W, \delta_{io}, \delta_{if}, \Delta\theta, (\Delta\theta)', C, \partial C/\partial\theta, Q, \partial Q/\partial\theta)$$

and in addition, the process may be based on the algorithm:

$$\Delta R = k_1 \int\int\int W(\partial C/\partial\theta)(\partial Q/\partial\theta)(\partial [\Sigma\{\delta_{io}-\delta_{if}\}]/\partial\theta) d\theta d\theta d\theta + k_2(\Delta\theta)\{(\Delta\theta)'\}$$

wherein $\partial C/\partial\theta$ represents the partial derivative of concentration of fragrance composition inhaled with respect to time; wherein $k_1$ and $k_2$ are constants of integration and wherein the term: $\Sigma\{\delta_{io}-\delta_{if}\}$ is a summation in units of microvolts for M back, shoulder and/or neck muscles where $1 \leq M \leq M_{max}$ with $M_{max}$ being the maximum number of back, shoulder and neck muscles in a human mammal.

As used herein the fragrances of rose, floral, musky, ambery, sweet and or powdery is understood to mean a fragrance composition that a person with ordinary skill in the art would recognize as having the characteristics of these well known fragrances. The fragrances of the invention are not limited to those fragrances that have these characteristics alone, but also includes fragrances as having these notes or nuances in the fragrances and which provide the muscle relaxing characteristics described herein.

More specifically, the fragrance compositions useful in the practice of our invention preferably contain hexahydro-4,6,6,7,8,8-hexamethylcyclopenta-γ-2-benzopyran, 1,4-dioxacyclohexadecane-5,16-dione, 1,2,3,4,5,6,7,8-octahydro-2,3,8,8-tetramethyl-2-acetonaphthone, benzyl acetate, 7-acetyl-1,1,3,4,4,6-hexamethyltetralin, benzyl salicylate, hexyl cinnamic aldehyde, 4-(4-hydroxy-4-methylpentyl)-3-cyclohexene-1-carboxaldehyde, tetrahydromuguol, p-t-butyl-α-methyldihydrocinnamic aldehyde, γ-methyl ionone, linalool, ethyl linalool, linalyl acetate, trans methyl dihydrojasmonate, heliotropine, coumarin, ethylene brassylate, ethyl vanillin, bergamot oil, β-phenylethylalcohol, citronellol, terpinyl acetate, 3-(2-isocamphenyl)cyclohexanol and γ-undecalactone.

Still more preferable, the aforementioned preferred fragrance components are to be contained in the fragrance compositions which are preferred for carrying out the process of our invention in the following ranges of weight percentages; and it is most preferred that the fragrance compositions useful in the practice of our invention contain at least 10 of the following ingredients in the stated ranges:

TABLE I

| INGREDIENT | WEIGHT PERCENTAGE RANGE |
|---|---|
| linalyl acetate | from about 1 to about 20% |
| linalool | from about 5 to about 40% |
| benzyl acetate | from about 5 to about 30% |
| 7-acetyl-1,1,3,4,4,6-hexamethyltetralin | from about 3 to about 25% |
| citronellol | from about 3 to about 8% |
| terpinyl acetate | from about 2 to about 6% |
| 3-(2-isocamphenyl)cyclohexanol | from about 1 to about 10% |
| hexahydro-4,6,6,7,8,8-hexamethylcyclopenta-γ-2-benzopyran | from about 5 to about 60% |
| benzyl salicylate | from about 10 to about 40% |
| hexyl cinnamic aldehyde | from about 5 to about 30% |
| 4-(4-hydroxy-4-methylpentyl)-3-cyclohexene-1-carboxaldehyde | from about 3 to about 20% |
| tetrahydromuguol | from about 3 to about 20% |
| p-t-butyl-α-methyldihydrocinnamic aldehyde | from about 2 to about 20% |
| γ-methyl ionone | from about 1 to about 20% |
| trans methyl dihydrojasmonate | from about 1 to about 40% |
| heliotropine | from about 1 to about 20% |
| coumarin | from about 1 to about 10% |
| ethylene brassylate | from about 1 to about 10% |
| ethyl vanillin | from about 1 to about 30% |
| 1,2,3,4,5,6,7,8-octahydro-2,3,8,8-tetramethyl-2-acetonaphthone | from about 1 to about 10% |
| 1,4-dioxacyclohexadecane-5,16-dione | from about 1 to about 20% |
| β-phenylethyl alcohol | from about 1 to about 5% |
| bergamot oil | from about 1 to about 10% |
| ethyl linalool | from about 1 to about 10% |
| γ-undecalactone | from about 1 to about 20% |

The fragrances of the present invention can be used in a wide variety of products. Suitable products include, but are not limited to, fine fragrances, colognes and nail care products; skin care products such as scented body sprays, bath products and body washes; skin tanning products such as lotions, sunscreens, gels, mousses, sprays, foams and creams; hair care products including shampoos, rinses, creams, foams conditioners, and sprays; laundry products such as detergents, fabric softeners, odorants, bleaches, brighteners; air fresheners, sachets, candles and the like.

Testing Protocol

Objective: To demonstrate that specific fragrance formulations provide back and/or shoulder and/or neck muscle relaxation during stress as compared with an unfragranced control.

Summary of Study: Three research studies were conducted, each using different fragrance formulations diluted in odorless diethyl phthalate (hereinafter referred to as DEP). Stress was induced in these research studies by means of the Stroop task. The Stroop task is a performance task that involves the naming of the typeface color of each of a series of words presented once per second on a computer screen when the words themselves are color names that conflict with the typeface color. The stress level of the task is enhanced at the 'halfway' point by moving the position of the word around on the screen and adding sound effects to each word presentation, such as breaking glass and screeching car brake effects. Subjects are also told that their performance is being tape-recorded, and a microphone is pointed out to them. The effect of a fragrance composition on the muscle is determined by comparing the muscle response to the Stroop task in a group of subjects who are exposed to the diluted fragrance composition by inhalation to a group of subjects who are exposed to the odorless diluent only.

Subjects: For the research studies subjects were right-handed female adults, aged 25-50, English first language, not currently taking prescribed medications (with the exception of birth control medications, anti-histamines and over-the-counter medications) and free of medical history of cardiovascular or other serious disease, and free of psychological/psychiatric history. The subjects had a median age of 41. In each study subjects were divided into two groups, a Fragrance group and a Control (DEP) group, as more particularly described herein.

Figure 1:
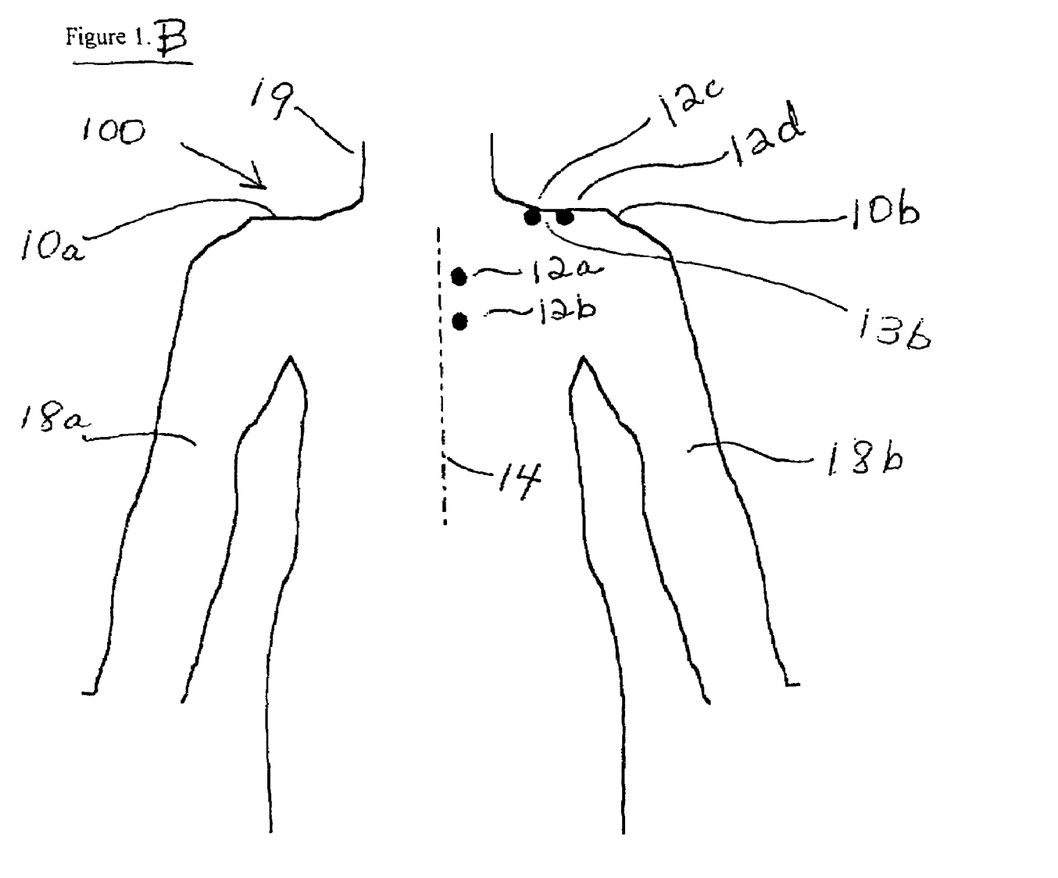
FIG. 1A and FIG. 1B are schematic diagrams of the back, rear shoulder and rear neck areas of a human torso indicating the locations of the placement of sensors on each participating subject in order to measure upper and lower Trapezius shoulder muscle electromyogram (EMG) muscle activity, as set forth in the "Testing Protocol", supra.
Figure 1A:
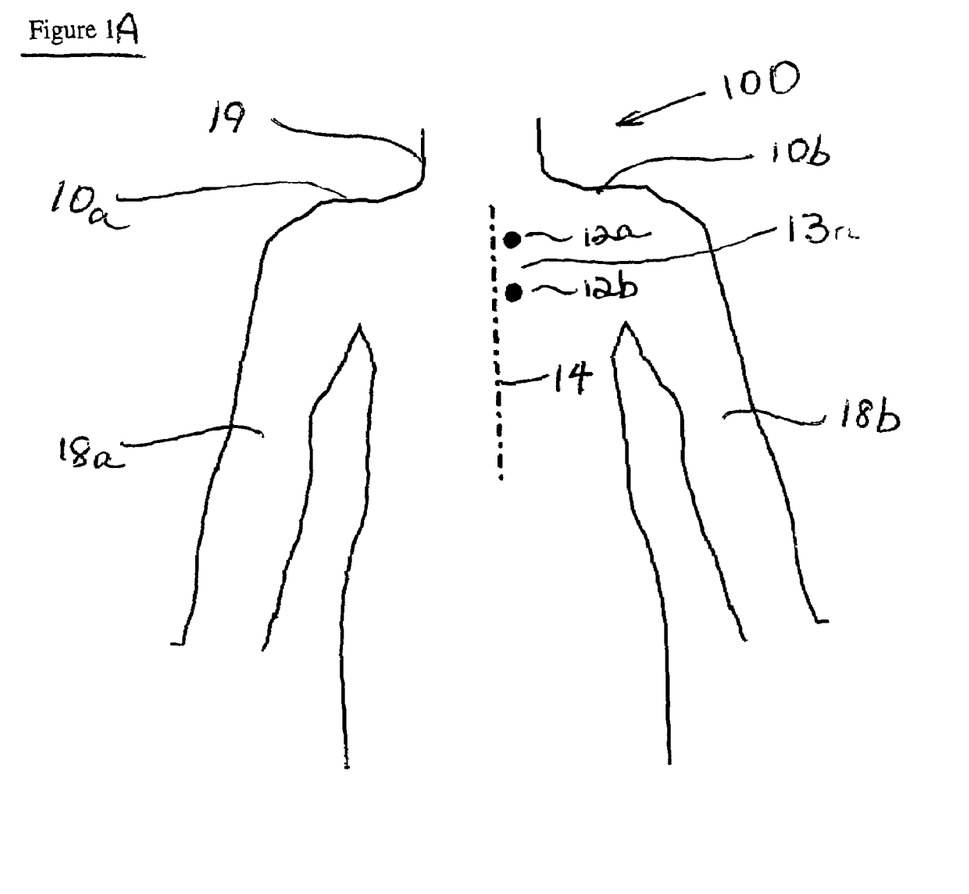

Experimental Protocol: The Fragrance group in Study 1 received Fragrance A (n=15), as more particularly described in Example I, herein. The Fragrance group in Study 2 received Fragrance B (n=20), as more particularly described in Example II, herein, or Fragrance C (n=20), as described in Example III, herein, or Fragrance D (n=20), as described in Example IV, herein. The Fragrance group in Study 3 received Fragrance E (n=5), as more particularly described in Example V, herein, or Fragrance F (n=7), as described in Example VI, herein. In Studies 1 (n=15), 2 (n=20), and 3 (n=6) the unfragranced Control group received only odorless DEP. In all three studies each subject was tested individually in a single session. Subjects were told the general nature and course of the study, namely: "how well people perform on different mental tasks in the presence and absence of fragrance. The fragrances in the study range anywhere between strong, moderate and weak, and none of them are unpleasant." For Studies 1 and 2 a measure of back and/or shoulder and/or neck muscle activity was taken from a pair of electrodes placed on the upper back, near the spine, as shown in FIG. 1A. For Study 3 an additional measure of back and/or shoulder and/or neck muscle activity was taken from a second pair of electrodes placed on the upper shoulder, as shown in FIG. 1B. Both placements lie on top of the large, fan-shaped Trapezius muscle, which connects the shoulder to the spine from the neck to the mid-back. The sensors measure the electromyogram (EMG) from underlying muscles, including the Trapezius and other deeper muscles, including but not limited to upper layer muscles such as the Splenius capitis muscle, the Splenius cervicus muscle, the Levator scapulae muscle, the Rhomboid major muscle, the Supraspinatus muscle, the Erector spinae muscle, the Trapezius muscle, the Serratus anterior muscle and the External oblique muscle; intermediate layer muscles such as the Rectus capitis posterior major muscle, the Longissimus captis muscle, the Spinalis thoracis muscle and the Iliocostalis lumborum muscle; and the deep layer muscles such as the Rectus capitis posterior minor muscle, the Interspinalis cervicis muscle, the Levator costae muscle, the Longus rotatores thoracis muscle and the Quadratus lumborum muscle.

After the sensor placement, the experimenter went to an adjoining room where the psychophysiology monitoring equipment, described herein, was located. The experimenter could view the subject through a one-way mirror. Initially there was a series of practice trials, lasting in total approximately 30 minutes, in which the procedures of the baselines and Stroop test were presented to subjects in order to allow them to adapt to the procedures. After this the experimenter entered the room and introduced the fragrance. Fragrance A was a fragrance composition diluted at 20% by weight in DEP. Fragrances B-F were all fragrance compositions diluted at 10% by weight in DEP. The Control substance was pure DEP. The experimenter uncovered a 250 ml wide-mouth jar filled with 100 ml of liquid and placed it about 1 meter in front of the subject on a table. A small fan was turned on next to the jar and pointing towards the subject, blowing across the top of the jar towards the subject.

For all studies the experiment consisted of a Rest period followed by the Stroop task period, followed by a Recovery period. Each period was 3 minutes in duration. The Rest period was a baseline condition in which each of the subjects observed a series of colored squares presented at an easy-to-follow rate of 10 sec. per stimulus. Each subject's task was merely to count the number of squares of a particular color. This relatively elementary task effectively allowed each of the subjects to rest yet insured that each of the subjects was alert. The Stroop task was the stress condition, as described herein. The Recovery period was essentially the same as the baseline Rest, in which subjects performed another elementary colored squares counting task. Study 2 and 3 contained an additional period not used in Study 1, namely an "Eyes-Open" (EO) Rest period of 3 minutes duration that preceded the baseline Rest period.

EMG recording and data analysis: Trapezius EMG was recorded using a J&J Physiolab 1-330 C-2 system (J & J Engineering Inc., 22797 Holgar Ct. NE, Poulsbo, Wash. 98370). EMG signals were integrated and averaged to provide a mean value (in microvolts) for each of the 3 minute epochs.

For each Study the epoch preceding the Rest period was compared statistically to the Rest period, and was found to be not significantly different (p's>0.3). In Study 1 this preceding period was a colored square recovery period (3 minutes in duration) from the practice Stroop task. In Studies 2 and 3 the preceding period was the "EO Rest" period. For Studies 1 and 2 the EMG activity during this preceding rest period was used as a covariate in a repeated measures analysis of covariance of the Rest, Stroop, and Recovery period means. Use of a covariate allows individual differences in resting value to be statistically removed from comparisons among conditions and between groups. This permits a more sensitive (statistically powerful) test of the treatment effects. Significance was set at the 0.1 level for the between-group difference or the between-group by condition interaction. The results of Study 3 were not statistically analyzed due to the small group sizes involved.

Figure 2:
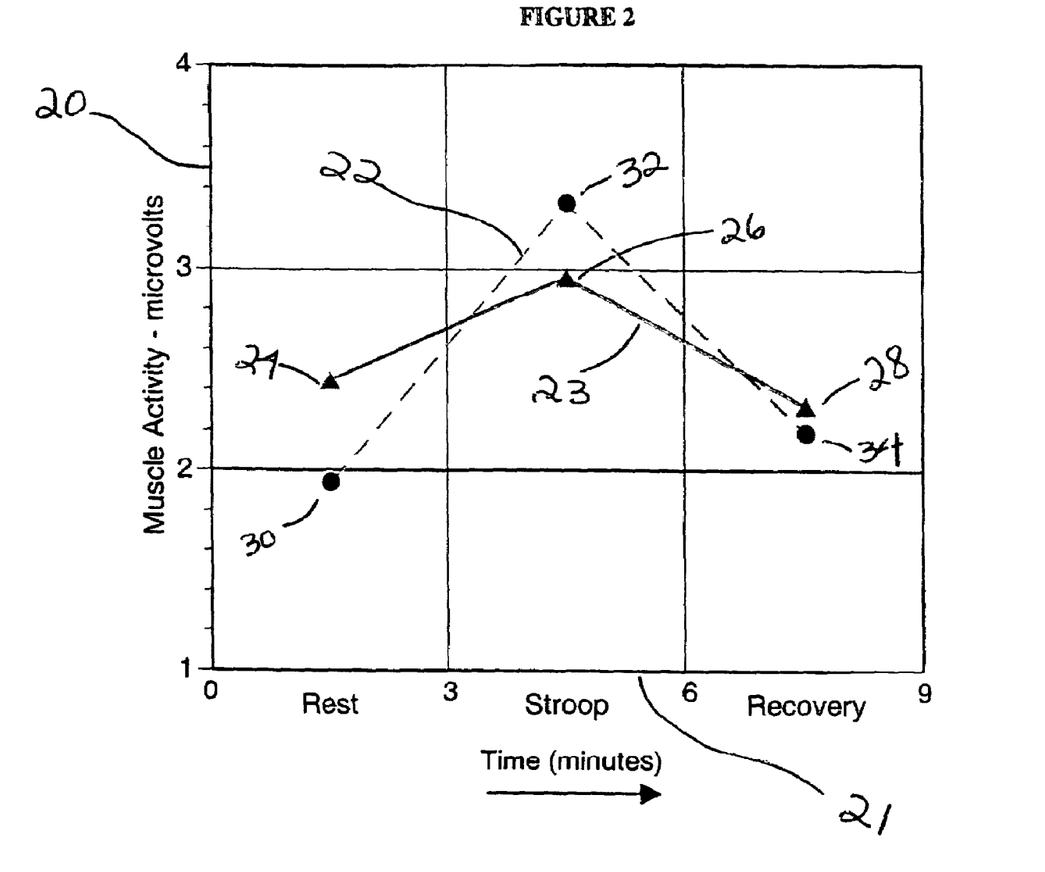
FIG. 2 is a set of graphs of muscle activity as measured in microvolts vs. time for the 3 minute Rest period, the 3 minute Stroop task period and for the 3 minute Recovery period when testing Fragrance A of Example I in a 20% DEP solution compared to a pure DEP control.

Study 1 and 2 Results: The Group X Period interaction was significant for Study 1 comparing Fragrance A to DEP (F[2, 25]=2.81, p=0.079) and for Study 2 comparing Fragrance B to DEP (F[2, 36]=2.53, p=0.094). As shown in FIG. 2, described herein, in FIG. 3, described herein, and in Table 2, herein, the Fragrance condition demonstrated reduced stress-reactive EMG increases as compared with the unfragranced Control condition. For Fragrance A, this reduction was 62.6% and for Fragrance B, this reduction was 39.6%. In contrast, Fragrance C and Fragrance D actually increased the stress-reactive EMG tensive response compared to DEP, by 162.5% and 95.0%, respectively, as shown in FIG. 4, described herein, and in Table 2, herein.

Figure 5:
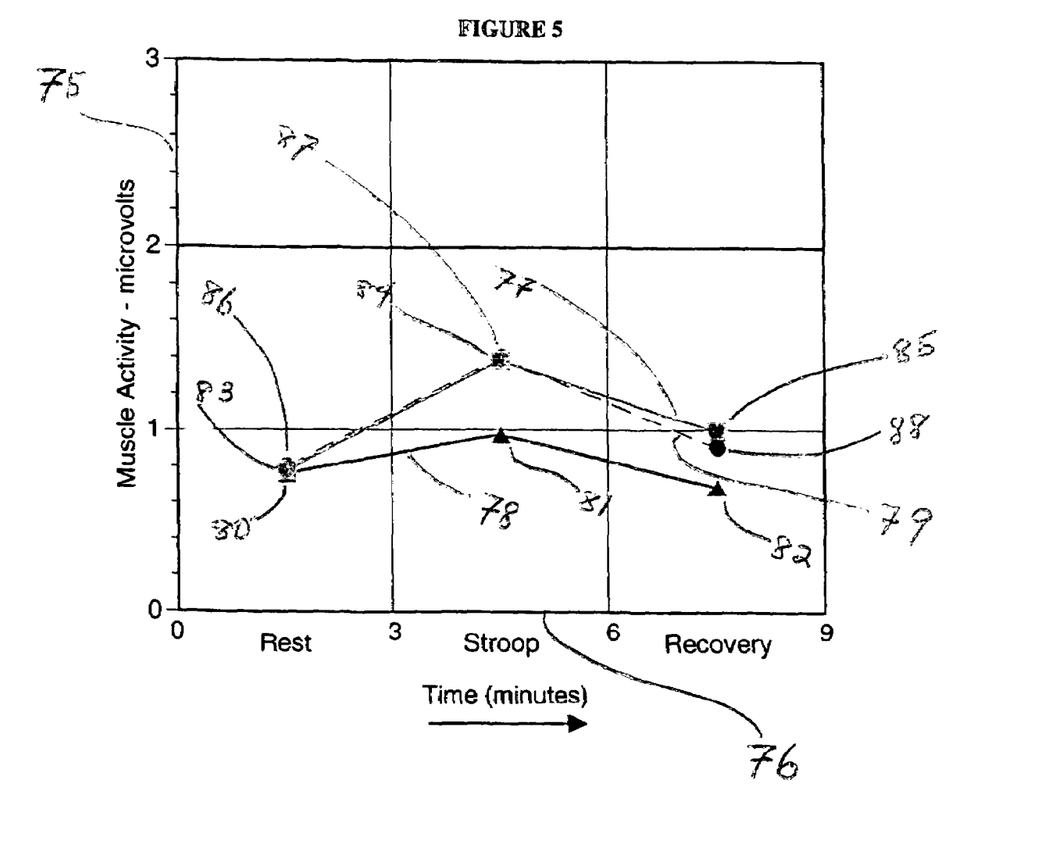
FIG. 5 is a set of graphs of lower Trapezius muscle activity as measured in microvolts vs. time for the 3 minute Rest period, the 3 minute Stroop task period and for the 3 minute Recovery period when testing Fragrance E of Example V and Fragrance F of Example VI, each in a 10% DEP solution compared to a pure DEP control.
Figure 6:
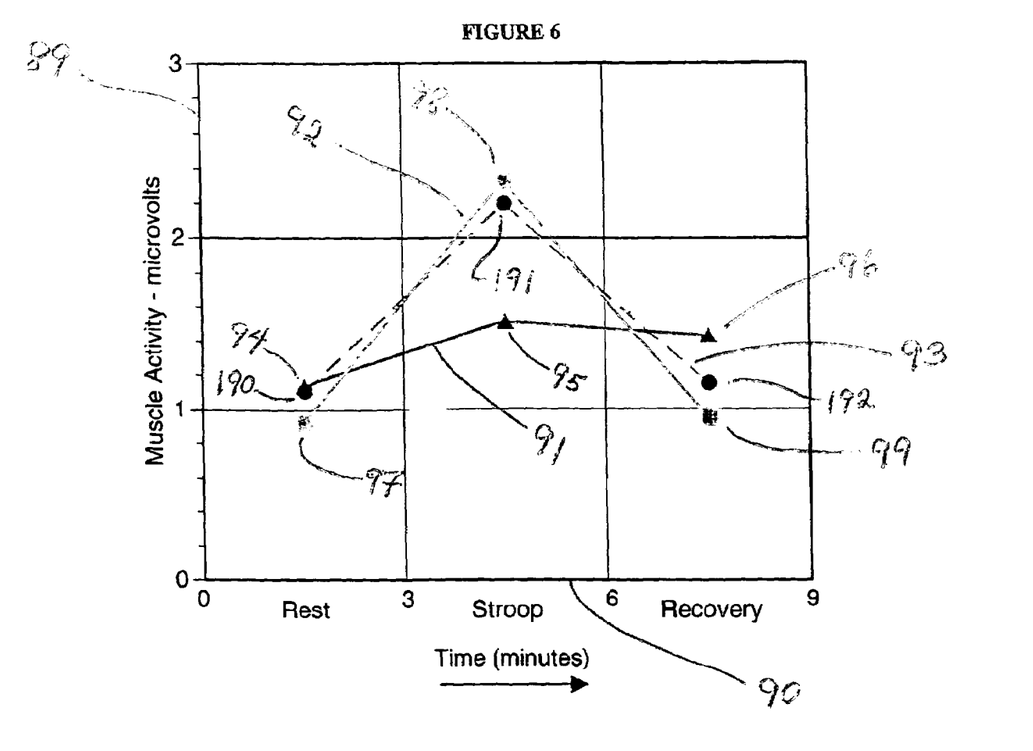
FIG. 6 is a set of graphs of upper Trapezius muscle activity as measured in microvolts vs. time for the 3 minute Rest period, the 3 minute Stroop task period and for the 3 minute Recovery period when testing Fragrance E of Example V and Fragrance F of Example VI, each in a 10% DEP solution compared to a pure DEP control.

Study 3 Results: These results are based on a small sample size (n<10), hence statistical analysis was limited to inspection of means. Fragrance E lowered both upper and lower Trapezius muscle stress-reactive tensive activity by 65.3% and 64.7%, respectively, as shown in FIG. 5 and FIG. 6, described herein, and in Table 3, herein. Fragrance E thus effects relaxation for both the upper Trapezius and lower Trapezius muscles. In contrast, Fragrance F increased the stress-reactive EMG tensive response compared with DEP for both the upper and lower Trapezius muscles by 28.5% and 0.8% respectively as shown in FIG. 5 and in FIG. 6 described herein and in Table 3, herein.

TABLE 2

Studies 1 and 2 Experimental means, adjusted for covariate, and stress reactivities of Lower Trapezius muscle (microvolts EMG)

Fragrance A - Study 1

| Task | DEP | Fragrance A |
|---|---|---|
| Rest | 1.93 | 2.44 |
| Stroop | 3.32 | 2.96 |
| Recovery | 2.18 | 2.32 |
| Reactivity (Stroop − Rest) | 1.39 | 0.52 |
| Diff Reactivity (Frag − DEP) | −0.87 | |
| % Diff Reactivity (Frag − DEP)/DEP | −62.6% | |

Fragrance B - Study 2

| Task | DEP | Fragrance B |
|---|---|---|
| Rest | 1.74 | 1.66 |
| Stroop | 2.27 | 1.98 |
| Recovery | 1.52 | 1.65 |
| Reactivity (Stroop − Rest) | 0.53 | 0.32 |
| Diff Reactivity (Frag − DEP) | −0.21 | |
| % Diff Reactivity (Frag − DEP)/DEP | −39.6% | |

Fragrance C - Study 2

| Task | DEP | Fragrance C |
|---|---|---|
| Rest | 1.79 | 1.80 |
| Stroop | 2.30 | 3.11 |
| Recovery | 1.55 | 1.55 |
| Reactivity (Stroop − Rest) | 0.50 | 1.32 |
| Diff Reactivity (Frag − DEP) | 0.82 | |
| % Diff Reactivity (Frag − DEP)/DEP | 162.6% | |

Fragrance D - Study 2

| Task | DEP | Fragrance D |
|---|---|---|
| Rest | 1.79 | 1.43 |
| Stroop | 2.30 | 2.40 |
| Recovery | 1.55 | 1.62 |
| Reactivity (Stroop − Rest) | 0.50 | 0.98 |
| Diff Reactivity (Frag − DEP) | 0.476 | |
| % Diff Reactivity (Frag − DEP)/DEP | 95.0% | |

TABLE 3

Study 3 Experimental means, adjusted for covariate, and stress reactivities of Lower and Upper Trapezius muscle (microvolts EMG)

Fragrance E

| | Lower Trapezius | | Upper Trapezius | |
|---|---|---|---|---|
| Task | DEP | Fragrance E | DEP | Fragrance E |
| Rest | 0.80 | 0.76 | 1.10 | 1.13 |
| Stroop | 1.40 | 0.97 | 2.20 | 1.51 |
| Recovery | 0.90 | 0.69 | 1.15 | 1.43 |
| Reactivity (Stroop − Rest) | 0.60 | 0.21 | 1.10 | 0.38 |
| Diff Reactivity (Frag − DEP) | −0.39 | | −0.72 | |
| % Diff Reactivity (Frag − DEP)/DEP | −64.7% | | −65.3% | |

Fragrance F

| | Lower Trapezius | | Upper Trapezius | |
|---|---|---|---|---|
| Task | DEP | Fragrance F | DEP | Fragrance F |
| Rest | 0.80 | 0.78 | 1.10 | 0.92 |
| Stroop | 1.40 | 1.38 | 2.20 | 2.33 |

TABLE 3-continued

Study 3 Experimental means, adjusted for covariate, and stress
reactivities of Lower and Upper Trapezius muscle (microvolts EMG)

| | | | | |
|---|---|---|---|---|
| Recovery | 0.90 | 0.99 | 1.15 | 0.95 |
| Reactivity (Stroop − Rest) | 0.60 | 0.60 | 1.10 | 1.41 |
| Diff Reactivity (Frag − DEP) | 0.00 | | 0.31 | |
| % Diff Reactivity (Frag − DEP)/DEP | 0.8% | | 28.5% | |

DETAILED DESCRIPTION OF THE DRAWINGS

Referring to FIG. 1A, for the lower Trapezius muscle, the locations 12a and 12b of placement of the sensors on a participating subject having torso 100 with neck 19 and shoulders 10a and 10b is such that the spacing between the electrodes at 12a and 12b is 4.5 cm. apart, center-to-center, and a distance of about 4 centimeters from the spine 14 of the torso 100. The midpoint between the electrodes is aligned horizontally with the vertical midpoint of the shoulder blade (scapula). The region of the lower Trapezius muscle is indicated by reference number 13a.

Referring to FIG. 1B for the upper Trapezius muscle, the spacing between electrodes 12c and 12d is about 2.5 cm. The midpoint of the electrode pair, 12-12d is placed 40% of the distance from the top outer edge of the shoulder blade (acromion) to the seventh cervical vertebra (C7) following the standardization of Farina et al, "Standardising Surface Electromyogram Recordings for Assessment of Activity and Fatigue in the Human Upper Trapezius Muscle", *European Journal of Applied Physiology*, 2002, 86, 459-478. The left arm of the subject is indicated by reference numeral 18a and the right arm of the torso of the subject is indicated by reference numeral 18b. The region of the lower Trapezius muscle is indicated by reference numeral 13a. The region of the upper Trapezius muscle is indicated by reference numeral 13b.

FIG. 2 sets forth graphs 23 (for Formulation A) and 22 (for the DEP control), of lower Trapezius muscle activity (on the "y" axis, 20, measured in microvolts) vs. time (in minutes) for the Rest period, the Stroop task period, and the Recovery period (time being measured on the "x" axis, 21). The Rest period muscle activity data point for Fragrance A is indicated by reference numeral 24. The Stroop task period muscle activity data point for Fragrance A is indicated by reference numeral 26. The Recovery period muscle activity data point for Fragrance A is indicated by reference numeral 28. The Rest period muscle activity data point for DEP is indicated by reference numeral 30. The Stroop task period muscle activity data point for DEP is indicated by reference numeral 32. The Recovery period muscle activity data point for DEP is indicated by reference numeral 34.

Figure 3:
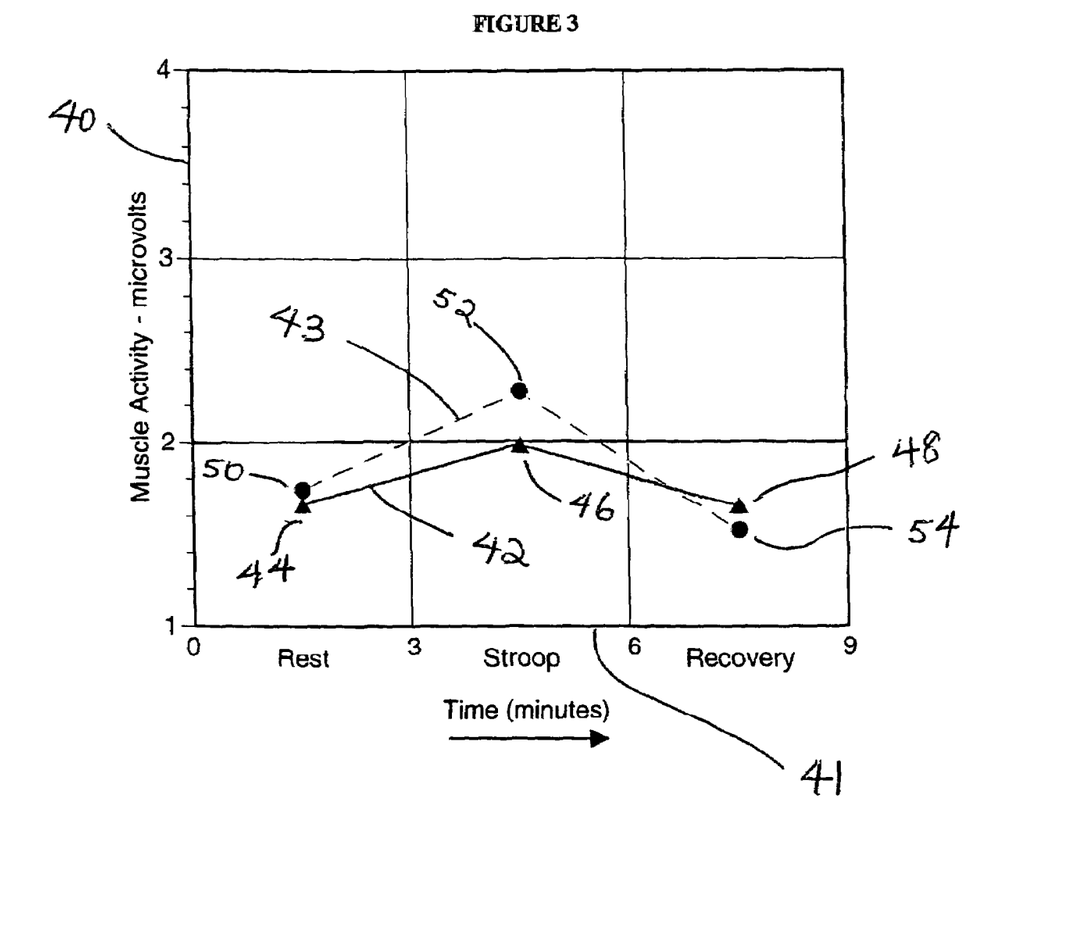
FIG. 3 is a set of graphs of muscle activity as measured in microvolts vs. time for the 3 minute Rest period, the 3 minute Stroop task period and for the 3 minute Recovery period when testing Fragrance B of Example II in a 10% DEP solution compared to a pure DEP control.
Figure 4:
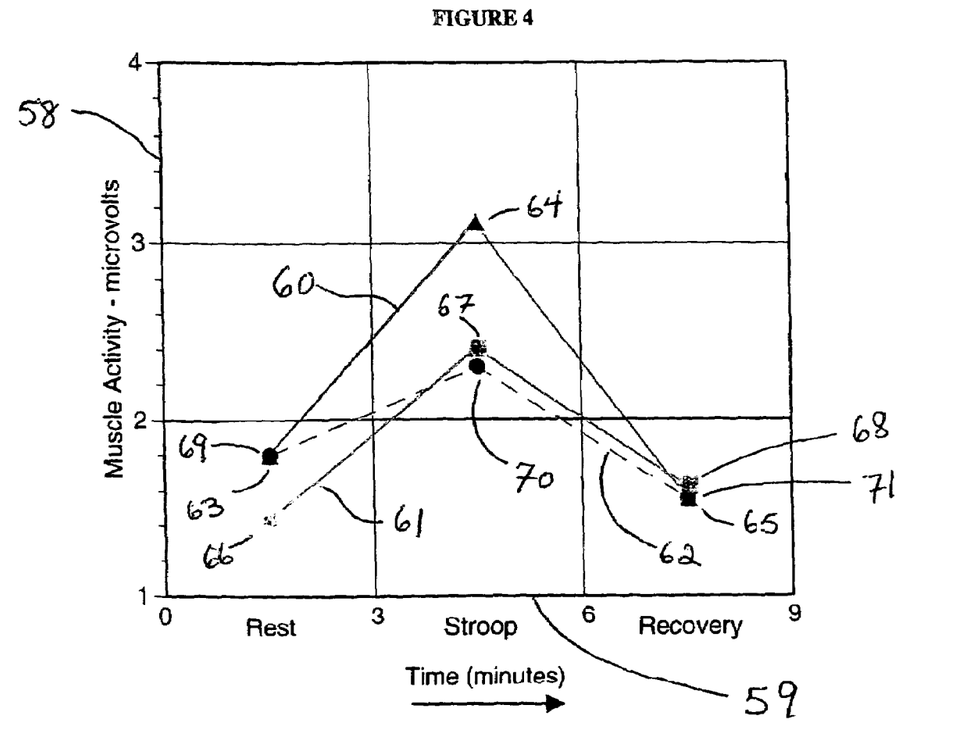
FIG. 4 is a set of graphs of muscle activity as measured in microvolts vs. time for the 3 minute Rest period, the 3 minute Stroop task period and for the 3 minute Recovery period when testing Fragrance C of Example III, and Fragrance D of Example IV, each in a 10% DEP solution compared to a pure DEP control.

FIG. 3 sets forth graphs 42 (for Formulation B) and 43 (for the DEP control), of lower Trapezius muscle activity (on the "y" axis, 40, measured in microvolts) vs. time (in minutes) for the Rest period, the Stroop task period, and the Recovery period (time being measured on the "x" axis, 41). The Rest period muscle activity data point for Fragrance B is indicated by reference numeral 44. The Stroop task period muscle activity data point for Fragrance B is indicated by reference numeral 46. The Recovery period muscle activity data point for Fragrance B is indicated by reference numeral 48. The Rest period muscle activity data point for DEP is indicated by reference numeral 50. The Stroop task period muscle activity data point for DEP is indicated by reference numeral 52. The Recovery period muscle activity data point for DEP is indicated by reference numeral 54.

FIG. 4 sets forth graphs 60 (for Formulation C), 61 (for Formulation D) and 62 (for the DEP control), of lower Trapezius muscle activity (on the "y" axis, 58, measured in microvolts) vs. time (in minutes) for the Rest period, the Stroop task period, and the Recovery period (time being measured on the "x" axis, 59). The Rest period muscle activity data point for Fragrance C is indicated by reference numeral 63. The Stroop task period muscle activity data point for Fragrance C is indicated by reference numeral 64. The Recovery period muscle activity data point for Fragrance C is indicated by reference numeral 65. The Rest period muscle activity data point for Fragrance D is indicated by reference numeral 66. The Stroop task period muscle activity data point for Fragrance D is indicated by reference numeral 67. The Recovery period muscle activity data point for Fragrance D is indicated by reference numeral 68. The Rest period muscle activity data point for DEP is indicated by reference numeral 69. The Stroop task period muscle activity data point for DEP is indicated by reference numeral 70. The Recovery period muscle activity data point for DEP is indicated by reference numeral 71.

FIG. 5 sets forth graphs 78 (for Formulation E), 77 (for Formulation F) and 79 (for the DEP control), of lower Trapezius muscle activity (on the "y" axis, 75, measured in microvolts) vs. time (in minutes) for the Rest period, the Stroop task period, and the Recovery period (time being measured on the "x" axis, 76). The Rest period muscle activity data point for Fragrance E is indicated by reference numeral 80. The Stroop task period muscle activity data point for Fragrance E is indicated by reference numeral 81. The Recovery period muscle activity data point for Fragrance E is indicated by reference numeral 82. The Rest period muscle activity data point for Fragrance F is indicated by reference numeral 83. The Stroop task period muscle activity data point for Fragrance F is indicated by reference numeral 84. The Recovery period muscle activity data point for Fragrance F is indicated by reference numeral 85. The Rest period muscle activity data point for DEP is indicated by reference numeral 86. The Stroop task period muscle activity data point for DEP is indicated by reference numeral 87. The Recovery period muscle activity data point for DEP is indicated by reference numeral 88.

FIG. 6 sets forth graphs 91 (for Formulation E), 92 (for Formulation F) and 93 (for the DEP control), of upper Trapezius muscle activity (on the "y" axis, 89, measured in microvolts) vs. time (in minutes) for the Rest period, the Stroop task period, and the Recovery period (time being measured on the "x" axis, 90). The Rest period muscle activity data point for Fragrance E is indicated by reference numeral 94. The Stroop task period muscle activity data point for Fragrance E is indicated by reference numeral 95. The Recovery period muscle activity data point for Fragrance E is indicated by reference numeral 96. The Rest period muscle activity data point for Fragrance F is indicated by reference numeral 97. The Stroop task period muscle activity data point for Fragrance F is indicated by reference numeral 98. The Recovery period muscle activity data point for Fragrance F is indicated by reference numeral 99. The Rest period muscle activity data point for DEP is indicated by reference numeral 190. The Stroop task period muscle activity data point for DEP is indicated by reference numeral 191. The Recovery period muscle activity data point for DEP is indicated by reference numeral 192.

The following Examples I, II and V describe and demonstrate embodiments of fragrance compositions (or 'formulations') which are useful in practicing the process of our invention. The following Examples III, IV and VI describe and demonstrate, for purposes of comparison, embodiments of fragrance compositions (or 'formulations') which are not useful in practicing the process of our invention, and accordingly, which cannot be employed in practicing our invention. The examples are given solely for the purpose of illustration and are not to be construed as limitations of the present invention, as many variations thereof are possible without departing from the sprit and scope of the invention which is only limited by the claims, as set forth herein.

EXAMPLE I

Preparation of Fragrance A

Fragrance A is prepared by admixing the following ingredients having indicated weight percentages:

| INGREDIENT | WEIGHT PERCENTAGE |
|---|---|
| hexahydro-4,6,6,7,8,8-hexamethylcyclopenta-γ-2-benzopyran | 50% |
| benzyl salicylate | 16% |
| hexyl cinnamic aldehyde | 10% |
| 4-(4-hydroxy-4-methylpentyl)-3-cyclohexene-1-carboxaldehyde | 7% |

-continued

| INGREDIENT | WEIGHT PERCENTAGE |
|---|---|
| tetrahydromuguol | 5% |
| p-t-butyl-α-methyldihydrocinnamic aldehyde | 4% |
| γ-methyl ionone | 3% |
| trans methyl dihydrojasmonate | 2% |
| heliotropine | 2% |
| coumarin | 1% |

The resulting material, when utilized according to the testing protocol set forth herein, effects the results as set forth in FIG. 2, described herein. The resulting composition has a powdery, musky and sweet aroma with powdery topnotes and muguet, rose, and sweet vanilla undertones.

EXAMPLE II

Preparation of Fragrance B

Fragrance B is prepared by admixing the following ingredients having indicated weight percentages:

| INGREDIENTS | WEIGHT PERCENTAGE |
|---|---|
| trans methyl dihydrojasmonate | 33% |
| 1,4-dioxacyclohexadecane-5,16-dione | 15% |
| ethylene brassylate | 8% |
| p-t-butyl-α-methyldihydrocinnamic aldehyde | 8% |
| 4-(4-hydroxy-4-methylpentyl)-3-cyclohexene-1-carboxaldehyde | 8% |
| bergamot oil | 8% |
| 1,2,3,4,5,6,7,8-octahydro-2,3,8,8-tetramethyl-2-acetonaphthone | 6% |
| ethyl linalool | 6% |
| γ-methylionone | 4% |
| β-phenylethyl alcohol | 4% |

The resulting material, when utilized according to the testing protocol set forth herein, effects the results as set forth in FIG. 3, described herein. The resulting composition has a floral, sweet, powdery aroma with muguet and rose topnotes and musk, powdery and sweet undertones.

EXAMPLE III

Preparation of Fragrance C

Fragrance C is prepared by admixing the following ingredients having indicated weight percentages:

| INGREDIENT | WEIGHT PERCENTAGE |
|---|---|
| hexahydro-4,6,6,7,8,8-hexamethylcyclopenta-γ-2-benzopyran | 30% |
| trans methyl dihydrojasmonate | 20% |
| 1,2,3,4,5,6,7,8-octahydro-2,3,8,8-tetramethyl-2-acetonaphthone | 10% |
| p-t-butyl-α-methyldihydrocinnamic aldehyde | 8% |
| β-phenylethyl alcohol | 6% |
| ethylene brassylate | 6% |

-continued

| INGREDIENT | WEIGHT PERCENTAGE |
|---|---|
| bergamot oil | 6% |
| ethyl linalool | 5% |
| 2-methyl-3-(p-methoxyphenyl) propanal | 5% |
| linalyl acetate | 4% |

The resulting material, when utilized according to the testing protocol set forth herein, effects the results as set forth in FIG. 4, described herein. The resulting composition has a sweet, floral aroma with floral, citrusy, lemon and fruity topnotes and sweet vanilla undertones.

EXAMPLE IV

Preparation of Fragrance D

Fragrance D is prepared by admixing the following ingredients having indicated weight percentages:

| INGREDIENTS | WEIGHT PERCENTAGE |
|---|---|
| dihydromyrcenol | 30% |
| amyl salicylate | 20% |
| terpinyl acetate | 10% |
| citrus oil | 8% |
| p-t-butylcyclohexyl acetate | 6% |
| orange oil | 6% |
| patchouli oil | 6% |
| isobornyl acetate | 5% |
| coumarin | 5% |
| lavandin oil | 4% |

The resulting material, when utilized according to the testing protocol set forth herein, effects the results as set forth in FIG. 4, described above. The resulting composition has an intense citrus, sweet aroma with fruity, pineapple undertones.

EXAMPLE V

Preparation of Fragrance E

Fragrance E is prepared by admixing the following ingredients having indicated weight percentages:

| INGREDIENT | WEIGHT PERCENTAGE |
|---|---|
| linalool | 30% |
| benzyl acetate | 20% |
| linalyl acetate | 10% |
| hexahydro-4,6,6,7,8,8-hexamethylcyclopenta-γ-2-benzopyran | 8% |
| 7-acetyl-1,1,3,4,4,6-hexamethyl tetralin | 6% |
| citronellol | 6% |
| β-phenylethylalcohol | 5% |
| ethyl vanillin | 5% |
| terpinyl acetate | 4% |
| coumarin | 3% |
| 3-(2-isocamphenyl)cyclohexanol | 3% |

The resulting material, when utilized according to the testing protocol set forth herein, effects the results as set forth in FIG. 5 and FIG. 6 described above. The resulting composition has a sweet, floral jasmine, muguet), musk, woody aroma with citrusy, sweet topnotes and rose, sweet vanilla undertones.

EXAMPLE VI

Preparation of Fragrance F

Fragrance F is prepared by admixing the following ingredients having indicated weight percentages:

| INGREDIENT | WEIGHT PERCENTAGE |
|---|---|
| benzyl salicylate | 30% |
| trans methyl dihydrojasmonate | 18% |
| coumarin | 14% |
| dihydromyrcenol | 10% |
| cyclopentadecanolide | 8% |
| β-ionone | 4% |
| 3-methyl-5-phenyl-1-pentanol | 4% |
| α-methyl-3,4(methylenedioxy)-hydrocinnamaldehyde | 3% |
| trans, trans 1-(2,6,6-trimethyl-3-cyclohexen-1-yl)-2-buten-1-one | 3% |
| 2,4-dimethyl-3-cyclohexene-1-carboxaldehyde | 2% |
| linalyl acetate | 2% |
| vanillin | 2% |

The resulting material, when utilized according to the testing protocol set forth herein, effects the results as set forth in FIG. 5 and FIG. 6 described above. The resulting composition has a spicy, herbaceous aroma with floral, citrus topnotes and rose, sweet vanilla undertones.

What is claimed is:

1. A process for effecting the relaxation to the back, shoulder or neck muscle of a human mammal for a substantial period of time consisting essentially of the step of continuously or periodically administering to said human mammal through inhalation a stress reactivity-reducing, tensive back, shoulder or neck muscle-relaxing period of time a stress reactivity-reducing, tensive back, stress reactivity-reducing shoulder or stress reactivity-reducing neck muscle-relaxing quantity and concentration of one or more fragrance compositions of matter wherein the fragrance composition administered comprises methyl dihydrojasmonate, 1,4-dioxacyclohexadecane-5,16-dione, ethylene brassylate, p-t-butyl-α-methyldihydrocinnamic aldehyde, 4-(4-hydroxy-4-methylpentyl)-3-cyclohexene-1-carboxaldehyde, bergamot oil, 1,2,3,4,5,6,7,8-octahydro-2,3,8,8-tetramethyl-2-acetonaphthone, ethyl linalool, γ-methyl ionone and β-phenylethyl alcohol.

2. The process of claim 1 which is a process for effecting the relaxation to the back, shoulder or neck muscle of a human mammal having a weight, of from about 50 pounds up to about 300 pounds, each of which back, shoulder or neck muscle has an initial magnitude of tension as measured by the Stroop task period muscle activity, in the range of from about 0.5 microvolts up to about 10.0 microvolts, for a period of time, in the range of from about 1 minute up to about 24 hours, consisting essentially of the step of continuously or periodically administering to said human mammal through inhalation over a stress reactivity-reducing, tensive back, shoulder or neck muscle-relaxing period of time, in the range of from about 1 minute up to about 24 hours, a stress reactivity-reducing, tensive back, shoulder or neck muscle-relaxing (i) quantity, in the range of from about 6 nanograms up to about 500 micrograms, (ii) concentration, C of from about 1 nanogram per liter up to about 125 micrograms per liter, and (iii) inhalation rate, of from about 1 microgram/hour up to about 45 milligrams/hour, of fragrance compositions comprising methyl dihydrojasmonate, 1,4-dioxacyclohexadecane-5,16-dione, ethylene brassylate, p-t-butyl-α-methyldihydrocinnamic aldehyde, 4-(4-hydroxy-4-methylpentyl)-3 -cyclohexene-l-carboxaldehyde, bergamot oil, 1,2,3,4,5,6,7,8-octahydro-2,3,8,8-tetramethyl-2-acetonaphthone, ethyl linalool, γ-methyl ionone and β-phenylethyl alcohol and the resulting magnitude of back muscle tension, is in the range of from about 0.4 microvolts up to about 3.3 microvolts and wherein the initial muscle tension is greater than at least about 1.05 times the final magnitude of tension.

3. The process of claim 1 wherein the back, shoulder or neck muscle relaxed is the top layer Trapezius muscle.

4. The process of claim 2 wherein initial magnitude of tension is greater than at least about 1.10 times the final magnitude of tension.

5. The process of claim 2 wherein the initial magnitude of tension is greater than at least about 1.25 times the final magnitude of tension.

\* \* \* \* \*